(12) United States Patent
Nelson et al.

(10) Patent No.: US 11,510,693 B2
(45) Date of Patent: *Nov. 29, 2022

(54) FORCEPS WITH TISSUE STOPS

(71) Applicant: GYRUS ACMI, INC., Southborough, MA (US)

(72) Inventors: Jeffrey J. Nelson, Plymouth, MN (US); Zane R Ward, Prior Lake, MN (US); Laura B. Eliason, Salem, SC (US)

(73) Assignee: Gyrus ACMI, Inc., Westborough, MA (US)

( * ) Notice: Subject to any disclaimer, the term of this patent is extended or adjusted under 35 U.S.C. 154(b) by 439 days.

This patent is subject to a terminal disclaimer.

(21) Appl. No.: 16/585,165

(22) Filed: Sep. 27, 2019

(65) Prior Publication Data

US 2020/0022719 A1 Jan. 23, 2020

Related U.S. Application Data

(63) Continuation of application No. 15/679,637, filed on Aug. 17, 2017, now Pat. No. 10,485,566.

(51) Int. Cl.
*A61B 17/28* (2006.01)
*A61B 17/29* (2006.01)
(Continued)

(52) U.S. Cl.
CPC .......... *A61B 17/282* (2013.01); *A61B 17/285* (2013.01); *A61B 17/29* (2013.01);
(Continued)

(58) Field of Classification Search
CPC . A61B 17/22031; A61B 17/28; A61B 17/282; A61B 17/285; A61B 17/29; A61B 17/295; A61B 17/32; A61B 17/320092; A61B 17/3201; A61B 17/3205; A61B 17/3209; A61B 17/3211;
(Continued)

(56) References Cited

U.S. PATENT DOCUMENTS

| 2,114,695 A | 4/1938 | Anderson |
| 2,137,710 A | 11/1938 | Anderson |

(Continued)

FOREIGN PATENT DOCUMENTS

| CN | 204671207 U | 9/2015 |
| CN | 105530879 A | 4/2016 |
| CN | 109394306 A | 3/2019 |

OTHER PUBLICATIONS

U.S. Appl. No. 15/679,637 U.S. Pat. No. 10,485,566, filed Aug. 17, 2017, Forceps With Tissue Stop.

(Continued)

*Primary Examiner* — Melanie R Tyson
(74) *Attorney, Agent, or Firm* — Schwegman Lundberg & Woessner, P.A,

(57) ABSTRACT

Forceps that include a hand piece, a jaw assembly connected to the hand piece, and a web. The jaw assembly is moveable between an open position and a closed position. The web is adapted to block an anatomical feature from extending beyond a proximal end of a gripping section of the jaw assembly. The web remains generally stationary relative to the handpiece when the jaw assembly is moved between an open position and a closed position.

17 Claims, 3 Drawing Sheets

(51) Int. Cl.
*A61B 18/14* (2006.01)
*A61B 17/295* (2006.01)
*A61B 17/285* (2006.01)
*A61B 18/00* (2006.01)
*A61B 90/00* (2016.01)

(52) U.S. Cl.
CPC ........ *A61B 17/295* (2013.01); *A61B 18/1445* (2013.01); *A61B 17/2841* (2013.01); *A61B 2017/2926* (2013.01); *A61B 2017/2936* (2013.01); *A61B 2018/0063* (2013.01); *A61B 2018/00589* (2013.01); *A61B 2018/00601* (2013.01); *A61B 2018/1452* (2013.01); *A61B 2018/1455* (2013.01); *A61B 2090/033* (2016.02)

(58) Field of Classification Search
CPC ........... A61B 2017/2926; A61B 2017/320093; A61B 2017/320094; A61B 2017/32113; A61B 18/1442; A61B 18/1445; A61B 18/1447; A61B 2018/145; A61B 2018/1452; A61B 2018/1455; A61B 2018/1457
See application file for complete search history.

(56) References Cited

U.S. PATENT DOCUMENTS

| | | |
|---|---|---|
| 3,911,923 A | 10/1975 | Yoon |
| 3,920,021 A | 11/1975 | Hiltebrandt |
| 3,934,589 A | 1/1976 | Zimmer |
| 3,938,527 A | 2/1976 | Rioux |
| 4,003,380 A | 1/1977 | Wien |
| 4,005,714 A | 2/1977 | Hiltebrandt |
| 4,016,881 A | 4/1977 | Rioux et al. |
| 4,054,143 A | 10/1977 | Bauer |
| 4,085,756 A | 4/1978 | Weaver |
| 4,171,715 A | 10/1979 | Forsström |
| 4,393,872 A | 7/1983 | Reznik et al. |
| 4,418,692 A | 12/1983 | Guay |
| 4,671,274 A | 6/1987 | Sorochenko |
| 5,147,378 A | 9/1992 | Markham |
| 5,222,973 A | 6/1993 | Sharpe et al. |
| 5,258,006 A | 11/1993 | Rydell et al. |
| 5,445,638 A | 8/1995 | Rydell et al. |
| 5,458,598 A | 10/1995 | Feinberg et al. |
| 5,527,313 A | 6/1996 | Scott et al. |
| 5,562,702 A | 10/1996 | Huitema et al. |
| 5,569,269 A | 10/1996 | Hart et al. |
| 5,735,849 A | 4/1998 | Baden et al. |
| 5,800,449 A * | 9/1998 | Wales ................ A61B 18/1447 606/205 |
| 5,984,939 A | 11/1999 | Yoon |
| 6,419,675 B1 | 7/2002 | Gallo, Sr. |
| 6,605,104 B2 | 8/2003 | Sato et al. |
| 8,663,270 B2 | 3/2014 | Donnigan et al. |
| 9,339,327 B2 | 5/2016 | Koss |
| 9,579,118 B2 | 2/2017 | Strobl |
| 10,485,566 B2 * | 11/2019 | Nelson ............... A61B 18/1445 |
| 2014/0330273 A1 * | 11/2014 | Strobl .................... A61B 18/18 606/48 |
| 2015/0331443 A1 * | 11/2015 | Lamser ............. A61B 18/1445 74/532 |
| 2016/0113668 A1 | 4/2016 | Murdeshwar et al. |
| 2016/0278847 A1 * | 9/2016 | Batchelor ........... A61B 17/285 |
| 2019/0053818 A1 | 2/2019 | Nelson et al. |

OTHER PUBLICATIONS

"U.S. Appl. No. 15/679,637, 312 Amendment filed Sep. 27, 2019", 7 pgs.
"U.S. Appl. No. 15/679,637, Non Final Office Action dated Apr. 8, 2019", 12 pgs.
"U.S. Appl. No. 15/679,637, Notice of Allowance dated Jul. 15, 2019", 8 pgs.
"U.S. Appl. No. 15/679,637, PTO Response to Rule 312 Communication dated Oct. 18, 2019", 2 pgs.
"U.S. Appl. No. 15/679,637, Response filed Jun. 21, 2019 to Non Final Office Action dated Apr. 8, 2019", 12 pgs.
"Chinese Application Serial No. 201710873548.0, Office Action dated Oct. 12, 2020", w/English Translation, 18 pgs.
"Chinese Application Serial No. 201710873548.0, Response filed Feb. 20, 2021 to Office Action dated Oct. 12, 2020", with English Claims and machine translation, 28 pgs.

* cited by examiner

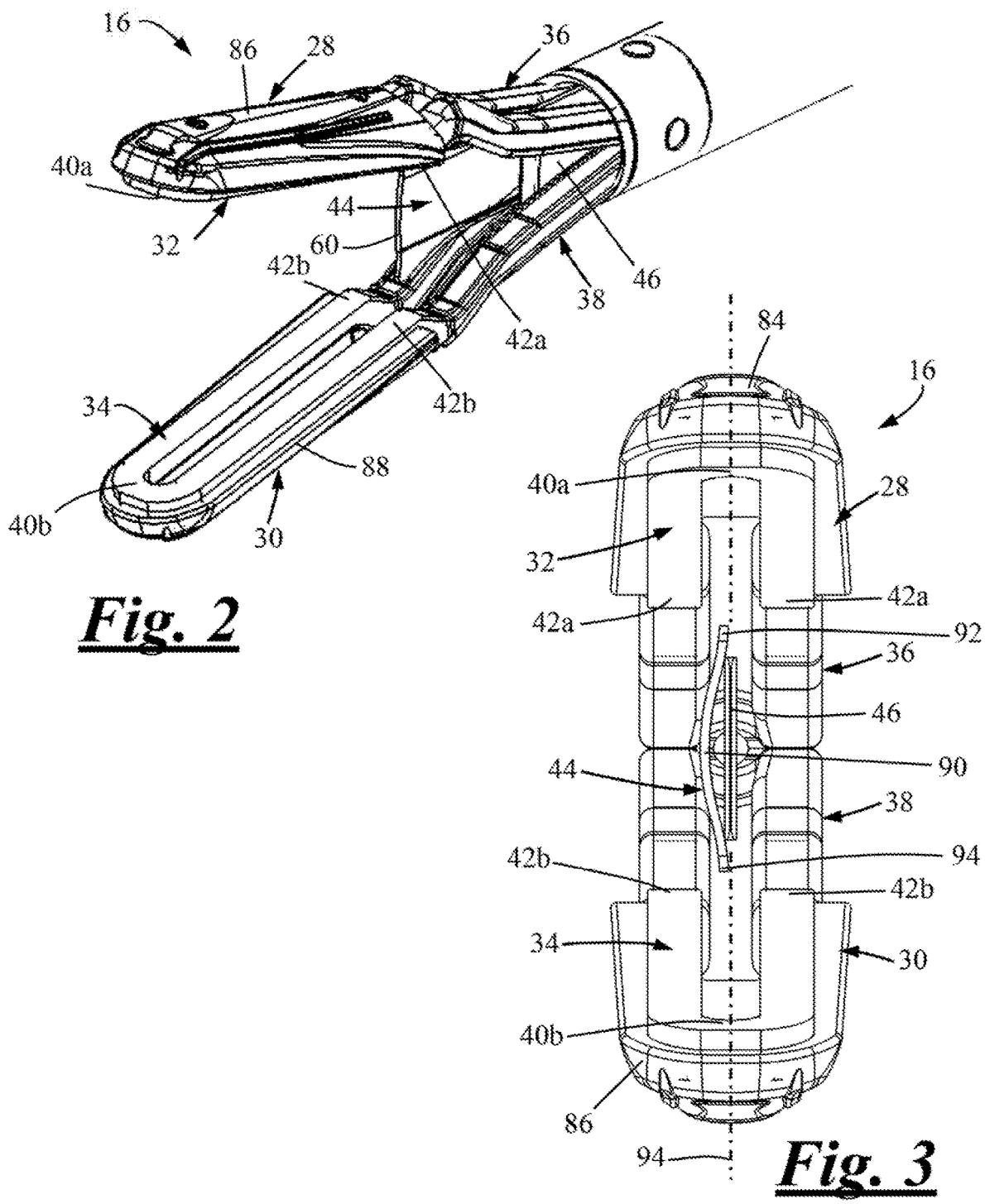

FORCEPS WITH TISSUE STOPS

FIELD

These teachings relate to an instrument, and more particularly to forceps that include a tissue stop.

BACKGROUND

Forceps are plier-like instruments that include a jaw assembly. The jaws of the jaw assembly can be used to effect an anatomical feature, such as a vessel or tissue. For example, a vessel or tissue can be positioned between the gripping sections of the jaws, and the jaws can be used to move, grip, grasp, push, pull, cut, dissect and/or otherwise effect the vessel or tissue. Some forceps also embody electrosurgical capabilities for electrically effecting an anatomical feature. For example, a vessel or tissue can be sealed or coagulated with an electrosurgical therapy current that is passed from or between one or both of the jaws.

Before effecting the anatomical feature with the jaw assembly, however, care should be taken to properly position or locate the anatomical feature between the gripping sections of the jaws. If a vessel or tissue is positioned between the jaws too far in a proximal direction, for example beyond a proximal end of the griping sections of the jaws, the vessel or tissue may not be held or gripped securely, which may undesirably cause trauma to the anatomical feature while being effected.

Further, while using electrosurgical forceps, if a vessel or tissue is positioned or located too far in a proximal direction, for example beyond the electrically conductive sections of one or both of the jaws, that portion of the vessel or tissue may not be sufficiently sealed or coagulated. Advancing a cut blade into or through a portion of a vessel or tissue that is not sufficiently coagulated may undesirably cause bleeding or trauma to the anatomical feature.

It may therefore be desirable to provide forceps that include a feature that can assist a user in positioning or locating an anatomical feature between the jaws. For example, it may be desirable to provide forceps that include a feature adapted to prevent, or at least reduce chances of an anatomical feature being positioned or located too far in a proximal direction between the jaws. It may be desirable to have a feature that is adapted to block an anatomical feature from extending beyond a proximal end of a gripping section of the jaw assembly. For example, it may be desirable to provide forceps that include a feature that can help locate an anatomical feature between the conductive sections of the jaws of electrosurgical forceps so that the entire anatomical feature can be properly sealed or coagulated.

SUMMARY

These teachings provide forceps that meet one or more of the aforementioned desires. For example, these teachings provide forceps with a feature that can assist a user in positioning or locating an anatomical feature between the jaws. Advantageously, these teachings provide forceps that include a feature adapted to prevent, or at least reduce chances to an anatomical feature being positioned or located too far in a proximal direction between the jaws. These teachings also provide forceps that include a feature that can help locate an anatomical feature between the conductive sections of the jaws of electrosurgical forceps so that the entire anatomical feature can be properly sealed or coagulated.

These teachings provide a tissue step. The tissue stop described herein may be referred to as a web. The web may function as a tissue stop. The web may advantageously assist a surgeon in positioning an anatomical feature between the jaws. The web may be a tissue stop that is adapted to block, prevent, or at least reduce chances of an anatomical feature being located too far in a proximal direction between the jaws. The web may be used to locate an anatomical feature between the gripping sections of the jaws and thus reduce the chances of some or all of the anatomical feature being pinched in a hinge or pivot mechanism of the forceps. The web may be used to locate an anatomical feature between the electrically conductive sections of the jaws so that the entire anatomical feature can be sufficiently coagulated during an electrosurgical procedure. By incorporating the web according to the teachings herein into a medical instrument such as a forceps, time spent ensuring an anatomical feature is properly positioned between the jaws may be reduced.

The web according to the teachings herein is provided between the jaws, but in a location that does not impede movement of a cut blade between the jaws. The web according to the teachings herein is provided between the jaws, and does not extend beyond a profile or outline of the jaws so that the forceps maintain a sleek and reduced profile, which may be desired in various medical procedures, such as laparoscopic procedures. That is, when the instrument is inserted into the anatomy through the trocar, because the tissue stop is located within a profile or outline of the jaws and/or introducer tube, the web does not catch or get snagged on the trocar or anatomy so that movement of the forceps is not impeded.

The web according to the teachings herein is provided at or near a proximal end of the gripping section(s) or electrically conductive section(s) of the jaw assembly so that the surface area of the gripping section is not reduced or taken up by a tissue stop, which thus advantageously allows for a maximum gripping surface area for gripping and effecting an anatomical feature.

BRIEF DESCRIPTION OF THE DRAWINGS

FIG. 2 is a perspective view of a portion of the jaw assembly.

FIG. 3 is a front view of the jaw assembly in an open position.

DETAILED DESCRIPTION

Figure 1:
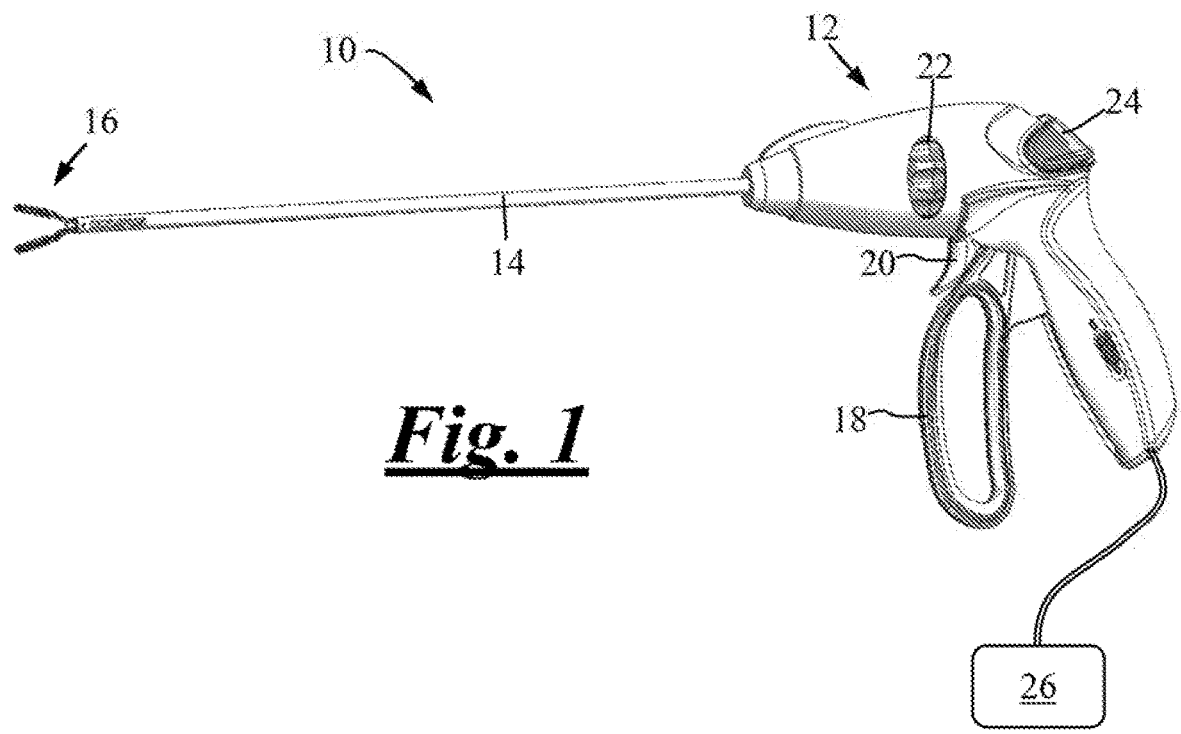
FIG. 1 is a perspective view of an instrument including a jaw assembly.

These teachings provide an instrument. The instrument can be any instrument for effecting an object. Effecting may mean, for example: manipulating, engaging, moving, grasping, gripping, pushing, pulling, cutting, tearing, coagulating, sealing, cauterizing, dissecting, fulgurating, or otherwise effecting an object or anatomical feature. The object may be any object, whether an anatomical feature or not. Exemplary anatomical features may include, for example, a vessel, tissue, vein, artery, any portion of the anatomy, or a combination thereof.

The instrument can be used in medically related procedures or in non-medically related procedures. The instrument can be used in open and/or laparoscopic or minimally invasive procedures. The instrument can be forceps, medical forceps, cutting forceps, electrosurgical forceps, bipolar forceps, the like, or a combination thereof.

The instrument may be used with or without power. When used with power, the instrument can be used in electrosurgery. The instrument can be in electrical communication with a suitable power source so that the instrument can be used in a bipolar circuit. For example, the jaws, gripping sections, electrically conductive sections, electrodes, the web, or a combination thereof may be adapted to pass a suitable current, therapy, and/or signal provided by a power source to electrically effect an anatomical feature. For example, the anatomical feature can be sealed or coagulated between the gripping sections or the electrically conductive sections of the opposing jaws with a bipolar therapy signal provided by the power source. That is, the opposing jaws of the instrument may be in communication with opposing poles of the power source so that the instrument can function as bipolar forceps and coagulate or seal an anatomical feature between the jaws. As will be discussed further below, the instrument also includes a cut blade that can be advanced through the coagulated or sealed anatomical feature. As will be discussed further below, in some configurations, the cut blade and/or the web may participate in an electrosurgical circuit with one or both of the jaws, or a remote electrode or patient pad, to electrically effect an anatomical feature.

The instrument may include a hand piece. The hand piece may function to house, support, and/or contain one or more components of the instrument. For example, the hand piece may house, support, and/or contain the parts or components required to move or actuate the jaw assembly, the one or more jaws, the cut blade, or a combination thereof. The hand piece may house, support, and/or contain the parts, components, electrical conductors or wires, required for the electrosurgical functions of the instrument. The instrument, the hand piece, or both may comprise the power source. The instrument, the hand piece, or both may include sufficient user controls for operating, actuating, and/or manipulating the instrument.

The instrument may include one or more user controls. The user controls may include a wheel, a trigger, a lever, a button, the like, or a combination thereof. One or more of these controls may be manipulated or moved to open/close the jaw assembly; move both jaws towards or away from each other; move one of the jaws towards or away from the other, opposing stationary jaw; rotate the jaw assembly; advance or retract the introducer; advance or retract a cut blade; apply a therapy current; or a combination thereof.

For example, manipulation or movement of the lever may be adapted to move the jaw assembly (i.e., move one or both of the jaws) from an open position to a closed position, and vice versa. For example, manipulation or movement of the wheel may be adapted to rotate the jaw assembly and/or the cut blade about a longitudinal axis of the introducer. For example, manipulation or movement of the trigger may be adapted to translate or reciprocate the cut blade along a longitudinal axis of the cut blade or the introducer. For example, manipulation or movement of the button may be adapted to apply a therapeutic current or signal from the power supply to the jaw assembly, one or both of the jaws, one or more of the gripping sections, one or more of the electrically conductive sections, the web, one or more electrodes, or a combination thereof, to electrically effect an anatomical feature.

The introducer may function to permit a portion of the instrument to be inserted into a patient or the anatomy, while a portion of the instrument remains outside of the patient or anatomy. The introducer may be configured to be inserted into the anatomy through a trocar or other opening in the anatomy. The introducer may allow for the jaw assembly and/or one or more functional elements of the instrument to be manipulated without being impeded by a trocar, the anatomy, or both.

The introducer may be an elongated member that extends along a longitudinal axis. The introducer may also be referred to as a tubular member. A proximal end of the introducer may be connected to the hand piece. A distal end of the introducer may define a mouth or opening (i.e., a distal opening). The introducer may be at least partially hollow and may define therein an inner portion. The hollow or inner portion of the introducer, the distal opening, or both, may be sufficiently sized so that one or more jaws, a jaw assembly, a cut blade, one or more webs or tissue stops, flexing or arcuate portions/sections of the jaw assembly, or a combination thereof can be at least partially received in and/or moved in the introducer. The opening or cross section of the introducer may be approximately the same size or slightly smaller than a height or cross section of the web so that a profile, size, cross section, or height of the web does not extend beyond a profile, size, cross section, or diameter of the introducer. This means that web does not project outside of, above, below, to the left, to the right, or a combination thereof of the introducer, jaw assembly, and/or the jaws. This advantageously ensures that the web does not get caught up on, contact, or interfere with the surrounding anatomy when the instrument is being moved through the anatomy to a site of interest. The introducer may be substantially straight; may include one or more angles, bends or arcs; or a combination thereof. The introducer may be substantially rigid, substantially flexible, substantially resilient, or a combination thereof.

The introducer can be moved (i.e., axially, distally, proximally, rotationally or a combination thereof) relative to the jaw assembly, the web, the flexing portions of the jaw assembly, the hand piece, or a combination thereof. The introducer can be moved by manipulating one or more of the user controls on the hand piece. The introducer may be moved relative to the jaw assembly, the hand piece, the web, or a combination thereof so that the jaw assembly can be moved or flexed between an open position and a closed position. More specifically, by manipulating one or more user controls, like the lever, for example, the introducer can be moved in a first axial direction along a longitudinal axis of the introducer (i.e., distally relative to the hand piece) and up, over and/or onto the flexing or arcuate portions of one or both of the jaws and thus apply a force onto the flexing or arcuate portions so that the jaw assembly can be moved into a closed or gripping position. By manipulating one or more user controls, the introducer can be moved in a second direction (i.e., proximally relative to the hand piece) so that the tubular moves off of the flexing portions, and thus remove the force from the flexing or arcuate portions thus allowing one or both of the jaws to relax or flex or move away from one another and into an open position. The open position may be a steady state position. The closed position may be a stead state position.

In some configurations, the introducer may be fixed or not-moveable relative to the hand piece, while one or both of the jaws, the jaw assembly, the anchoring sections, the web, or a combination thereof are moveable relative to the introducer and/or hand piece. In such configurations, one or both of the jaws, the jaw assembly, the anchoring sections, the web, or a combination thereof can be moved relative to the stationary introducer and/or hand piece by manipulating one or more of the user controls on the hand piece. One or both of the jaws, the jaw assembly, the anchoring sections, the web, or a combination thereof can be moved relative to the hand piece or introducer so that the jaw assembly can be moved or flexed between an open position and a closed position. More specifically, by manipulating one or more user controls, like the lever, for example, one or both of the jaws, the jaw assembly, the anchoring sections, the web, or a combination thereof can be moved or pulled in a first axial direction along a longitudinal axis of the introducer (i.e., distally relative to the hand piece and/or introducer) so that the opening at the distal end of the introducer engages or contacts the flexing or arcuate portions of one or both of the jaws, which thus applies a force onto the flexing or arcuate section(s) so that the jaw assembly can be moved into a closed or gripping position. By manipulating one or more user controls, one or both of the jaws, the jaw assembly, the anchoring sections, the web, or a combination thereof can be moved in a second direction (i.e., proximally relative to the hand piece and/or introducer) so that the tubular portion is moved off of or disengages the flexing portions, thus removing the force from the flexing or arcuate section(s) thus allowing one or both of the jaws to relax or flex or move away from one another and into the open position.

The instrument may include a jaw assembly. The jaw assembly may be configured to perform one or more effecting functions. For example, the one or more effecting functions may include: capturing an object or anatomical feature; grasping an object or anatomical feature; providing a clamping force to secure an object or anatomical feature; providing retraction of an object or anatomical feature; providing a compression force across an object or anatomical feature captured in the jaw assembly; or a combination thereof. The anatomical feature may be, for example, a vessel, tissue, vein, artery, a portion of the anatomy, or a combination thereof. The jaw assembly may be used in electrosurgery to perform one or more electrically effecting functions, such as cutting, coagulating, cauterizing, dissecting, and/or fulgurating an object anatomical feature. The jaw assembly may comprise one or more jaws, one or more webs, one or more cut blades, or a combination thereof for performing, executing, and/or enhancing one or more of the aforementioned functions.

The jaw assembly may include one or more jaws. One or more of the jaws may be configured to perform one or more effecting functions. For example, the one or more effecting functions may include: capturing an object or anatomical feature; grasping an object or anatomical feature; providing a clamping force to secure an object or anatomical feature; providing retraction of an object or anatomical feature; providing a compression force across an object or anatomical feature captured in the jaw assembly; or a combination thereof. The one or more jaws may be used in electrosurgery to perform one or more electrically effecting functions, such as cutting, coagulating, cauterizing, dissecting, and/or fulgurating an object anatomical feature.

The jaw assembly may comprise two jaws. The two jaws may be arranged to oppose one another. The jaws may include an upper jaw and a lower jaw; a first jaw and a second jaw; or a combination thereof. The upper jaw may be identical to the lower jaw. That is, the geometry of the upper jaw may be the same as the geometry of the lower jaw. Alternatively, the opposing may not be identical. That is, the geometry of the upper jaw may be different from the lower jaw.

One or more of the jaws may be substantially rigid; substantially flexible; substantially resilient, or a combination thereof. That is, one or more of the jaws may have one or more sections that are substantially rigid; one or more sections that are substantially flexible; one or more sections that are substantially resilient, or a combination thereof. Preferably, at least one of the jaws or a portion thereof is bendable so that the jaw assembly can be moved between the open position and the closed position by applying a force on one or both of the jaws. Preferably, at least one of the jaws or portions thereof is resilient so that the jaws can be moved between the closed position and the open position by releasing a force from one or both of the jaws.

The jaws may be fabricated from any suitable material. Preferably, the jaws are fabricated from a material that is suitable for use in medical procedures, and is flexible, yet strong. For example, the jaw elements may be made from sheet metal or wire. The jaws may be formed by any suitable process, such as stamping, metal injection molding (MIM), or plastic injection molding, for example. The jaws may be fabricated from a material that can pass current so that one or more of the jaws can be used in electrosurgery. One or both of the jaws, or sections thereof, may be electrically conductive. One or both jaws, or sections thereof, may be non-electrically conductive. The jaws may be thermally insulating so that a thermal barrier can be provided between the jaws, the jaw assembly, or both. A thermally insulating jaw may be preferred in some applications so that thermal spread is limited or reduced. One or more sections of the jaws may be covered or coated in an insulating material so that electrical shorts can be prevented if the jaws come into contact with one another or another object or feature of the instrument or surrounding environment.

One or more of the jaws may be moved to put the jaw assembly into a closed position or an open position.

The closed or gripping position may be defined as a position or location of the jaws or the jaw assembly where virtually no gap, or only a slight gap, exists between the gripping sections, the electrically conductive sections, the jaws, or a combination thereof. In the closed position, a clamping or gripping force of the gripping sections, the electrically conductive portions, the jaws, or a combination thereof may be higher or larger than a clamping or gripping force between the gripping sections, the electrically conductive sections, the jaws, or a combination thereof when the jaws are in the open position.

The open position may be defined as a position of the jaws or the jaw assembly where a gap exists between the gripping sections, the electrically conductive portions, the jaws, or a combination thereof. In the open position, a clamping or gripping force of the gripping sections, the electrically conductive sections, the jaws, or a combination thereof may be less or lower than a clamping or gripping force between the gripping sections, the electrically conductive sections, the jaws, or a combination thereof when the jaws are in the closed position.

While the jaw assembly is in an open position, closed position, or in a position there between, the jaw assembly can be rotated relative to the hand piece or the introducer by manipulating or moving one or more of the user controls on the hand piece. Rotating the jaw assembly may provide for a user to alter an orientation or approach of the jaw assembly relative to an anatomical feature without having to twist or adjust the hand piece into a difficult or uncomfortable position, for example.

Each jaw may comprise a gripping section and an anchoring section.

One or both of the gripping sections may be used to effect an object or anatomical feature. A gripping section may be located at or near a distal end of a jaw. A gripping section may be located between an absolute distal end of a jaw and a corresponding distal end of a flexing section or the anchoring section.

A gripping section may include one or more areas having teeth, no teeth, projections, or a combination thereof. The one or more teeth or projections may be formed or cut into the jaw or gripping section by a suitable process or method, such as by grinding, electrical discharge machining, stamping, coining, etc. A gripping section may include one or more troughs between the teeth to separate one tooth from another. The one or more teeth may have sharp points to assist in grasping an anatomical feature. Alternatively, or in addition, the one or more teeth may have flattened tops to distribute forces associated with grasping forces so that the object or tissue, especially vessel walls, are not punctured or otherwise damaged when an object, vessel, or tissue is between the jaws in the closed position.

A gripping section may be electrically conductive. That is, a gripping section may include one or more electrically conductive sections. The electrically conductive section may function to pass one or more therapy signals or currents between the gripping section, electrically conductive section, an object, the anatomy, or a combination thereof. The electrically conductive section may be or include an electrode or may be in communication with a power source. The electrically conductive may be an entire portion of the gripping section. That is, the electrically conductive sections may extend in an area or region between a distal end or tip of a jaw and a distal portion of an arcuate section. In other configurations, the electrically conductive sections may comprise a smaller area or section than the entire gripping section. Preferably, the instrument is adapted to pass opposing bipolar voltages to the opposing gripping sections to provide sealing or coagulation of an anatomical feature located between the gripping sections so that the instrument can function as bipolar forceps.

The gripping section may comprise a plate. The plate may be fabricated from an electrically conductive material, such as sheet metal. The plate may be an electrode. The plate may be in electrical communication with the power source, and may function to pass a therapy current from the power source to or through an anatomical feature to another electrical conductor or plate, such as the web, for example, to electrically effect an anatomical feature located between the plates. The plate may be assembled onto an insulator, and the insulator may then be attached or assembled onto the jaw. The plate may include one or more features of the gripping section discussed above (i.e., teeth, no teeth, etc.).

A gripping section may include one or more insulated sections or non-electrically conductive sections. The one or more insulated or non-electrically conductive sections may be insulated or otherwise not connected to an electrode or power source. Accordingly, the one or more non-electrically conductive sections may be unable or restricted from passing a therapy current between the jaws, an object, the anatomy, or a combination thereof.

The anchoring section of a jaw may function to connect or attach the corresponding jaw to the hand piece. The anchoring section may function to connect or attach the corresponding jaw to the hand piece so that the jaws do not move relative to the hand piece. The anchoring section may function to connect or attach the corresponding jaw to the hand piece so that the jaws do not move axially (e.g., proximally and distally) relative to the hand piece. The anchoring section may function to connect or attach the corresponding jaw to the hand piece so that the jaws do not move axially (e.g., proximally and distally) relative to the hand piece, but allow for rotation of the corresponding jaw relative to the hand piece (e.g., rotation about a longitudinal axis of the introducer). The anchoring section may function to connect or attach the corresponding jaw to a corresponding mechanism in the hand piece so that the corresponding jaw moves (i.e., axially and/or rotationally) relative to the hand piece when one or more of the user controls are manipulated.

Each anchoring section may comprise a flexing section. The flexing sections may cooperate with the introducer to move the jaw assembly, the one or more jaws, or both, from an open position to a closed position and from a closed position to an open position. The flexing sections may be at least partially flexible and/or resilient so that the jaw assembly, the one or more jaws, or both can be moved, bent, pivoted, flexed into a closed position when a pressure or force is applied thereto. When the pressure or force is released or removed from the flexing sections, the flexing sections, the jaw assembly, the jaws, or a combination thereof can move, bend, flex or relax back to an open position. The open position may be a steady state position of the jaw assembly. The pressure may be a result of the introducer, the distal end of the introducer contacting the flexing section.

The one or more flexing sections can be any feature that is at least partially taller, wider, and/or larger than the introducer, an inner portion of the introducer, an opening of the introducer (e.g., the distal opening), or a combination thereof. For example, the one or more flexing sections can be a raised section or an arcuate-shaped section or a ramped or angled portion relative to the rest of the legs, or a combination thereof. The flexing section can be a thickened portion of the jaw or a projection attached to the jaw. The flexing section may be a section that draws away from or extends away from a corresponding gripping section or leg of the jaw. The flexing section may be located proximal of the gripping section.

In some configurations, rather than having jaws that flex and bend between the open and closed positions by applying or removing a force from one or more of the flexing sections, the jaw assembly or the jaws may include a hinge or pivot mechanism for pivoting the jaw assembly between the closed and open positions.

Each jaw or anchoring section may include legs. The legs may be elongated members that function to attach or connect a corresponding jaw to the hand piece. Each jaw may be defined by two or more adjacent legs. The legs may extend between the hand piece and the gripping section of a jaw. The legs may extend from the hand piece to a distal end of the jaw, and the gripping section can be a feature that is added to a distal portion of the legs to form the gripping section. The legs may be offset from one another so that a slot is defined therebetween.

Each jaw may include one or more slots. The slot may function to provide a passageway or area for one or more features of the instrument to be located. For example, a cut blade may be located in the slot. For example, a web may be located in the slot. For example, both a cut blade and a slot may be located in a slot. The slot may be substantially free of features or obstructions so that the cut blade, a web, or both can be located and/or moved therein. The slot may be defined between adjacent edges of two opposing legs that define a jaw.

The slot may be centered upon a central plane or axis of a jaw or the jaw assembly, or the slot may be offset or laterally spaced apart from a longitudinal axis to one side of the jaw or jaw assembly. The center plane or axis of the jaw or jaw assembly may be the axis or plane along which the jaw or jaw assembly moves between the open and closed position. The center plane or axis of the jaw or jaw assembly may be generally perpendicular to a longitudinal axis of the introducer. One of the cut blade and the web may be located at a center plane or axis of the slot, and another one of the cut blade and web may be laterally offset towards one of the adjacent edges of the legs defining the slot. Alternatively, both the cut blade and the web may be laterally offset from a center plane or axis of the slot towards opposing edges of the legs that define the slot. Alternatively, both the cut blade and the web may be laterally offset from a center plane or axis of the slot towards one of the legs that define the slot. The features inside the slot are preferably arranged in the slot such that the features do not interfere with one another.

The jaw may comprise one or more ribs. The one or more ribs may function to strengthen and/or reinforce the anchoring section, the legs, the jaw, or a combination thereof. The one or more ribs may extend between and/or connect the opposing legs. The one or more ribs may form a bridge over a corresponding slot defined between two adjacent legs of a jaw.

The one or more ribs may function to attach the web to one or more of the jaws and/or the anchoring sections. Preferably, the one or more ribs cooperate with one or more notches defined in the web to prevent movement of the web relative to one or both of the jaws; relative to the jaw assembly; relative to the hand piece; relative to the cut blade; or a combination thereof, even when one or both of the jaws, gripping sections, cut blade, or a combination thereof are moved.

Preferably, each jaw or anchoring section comprises one rib that cooperates with one corresponding notch defined in the web. The rib may be located anywhere along a length of the jaw, anchoring section, leg(s), etc.

When two jaws are assembled or arranged adjacent to one another to form the jaw assembly, two of the ribs may generally oppose each other. This means that the ribs are located in the same general axial location or position relative to the proximal end and distal ends of the jaws. Alternatively, the ribs may be offset relative to one another, meaning that one rib may be located further in a proximal or distal direction than another rib. Each jaw may include any number of ribs. For example, a jaw may include zero ribs, one or more ribs, two or more ribs, three or more ribs, etc.

Each jaw may include a jaw shroud. The jaw shroud may function to reinforce or stiffen the gripping section of a jaw. Preferably, the jaw shroud reinforces or stiffens a griping section of a jaw that is bendable and flexible so that the jaw is no longer bendable and flexible but instead rigid. Advantageously, a jaw shroud may provide for an entire jaw to be bendable or flexible so that the jaw can be bent or flexed between a closed and open position as was discussed above, while the gripping sections are made rigid or not bendable as the rest of the jaw so that an anatomical feature can be securely gripped between the jaws without the jaw deflecting or bending while in the closed position. The jaw shroud may function to provide the jaw assembly with a substantially uniform grasping or gripping pressure or force in the gripping section. The jaw shroud may function to overcome beam deflection in one or both of the jaws when the jaw assembly is in a closed position or is being moved into the closed position especially when an object, vessel, or tissue is located between the jaws.

The jaw shroud may be attached to a jaw in any suitable manner. For example, the jaw shroud may be bonded or over-molded onto a jaw. For example, the jaw shroud can be slipped-on or slipped-over a distal end of a jaw. For example, the jaw shroud may be attached, connected, interlaced, welded, ultrasonically welded, staked, adhered, or a combination thereof onto a jaw. For example, the jaw shroud can be snapped into or onto a channel, groove, or projection in or on a corresponding jaw. The jaw shroud can include one or more connecting features that may cooperate with one or more undercut features on the jaw. The one or more connecting features, undercut features, or both can be welded or melted together to prevent or restrict removal or separation of the jaw shroud and the jaw. The one or more connecting features, undercut feature, or both may be one or more metal or plastic mating projections, grooves, nubs, posts; mating male and female dovetail sections, or other like features suitable for connecting the spine and the shroud.

In some configurations, the jaw shroud may be irreversibly attached to the jaw. Irreversibly attached may mean that the jaw cannot be separated from the jaw without substantially damaging the jaw shroud and/or the jaw. In some configurations, the jaw shroud may be integrally formed with the jaw.

The jaw shroud may be fabricated from a suitable material. Preferably, the jaw shroud is fabricated from a material that is suitable for use in medical procedures, such as metal and/or plastic, for example. The jaw shroud may be formed by any suitable process, such as stamping, metal injection molding (MIM), or plastic injection molding, for example. The jaw shroud may be thermally insulating so that a thermal barrier can be provided between the jaws, the jaw assembly, or both. A thermally insulating shroud may be preferred in some applications so that thermal spread is limited or reduced. The jaw shroud may be electrically insulating to prevent an electrical short when the instrument is used in electrosurgery.

The instrument may include one or more webs. Advantageously, the web may function to block, prevent, or at least restrict an object or anatomical feature from being positioned or extending beyond a proximal end of a gripping section. Advantageously, the web may block, prevent, or restrict an anatomical feature or object from extending into a hinge, joint or pivot mechanism of the jaw assembly thus reducing chances of an anatomical feature being pinched therein when the jaw assembly is moved or flex between open and closed positions. Advantageously, the web may block, prevent or restrict an anatomical feature from extending into an area where the flexing sections are (i.e., beyond a distal end of the flexing sections). Advantageously, the web may block, prevent, or restrict an anatomical feature from extending too far in a proximal direction and off of a gripping section thus ensuring that a sufficient gripping force is applied on a desired portion of the anatomical feature. Advantageously, the web may block, prevent or restrict an anatomical feature or object from extending too far in a proximal direction and off of an electrically conductive section thus ensuring that an entire desired portion of the anatomical can be electrically coagulated during an electrosurgical procedure.

The web may be located in one or both of the slots defined in the anchoring sections of two jaws. The web may be generally centered in one or both of the slots (i.e., arranged along a central plane of the slot(s) or gripping section or jaw assembly or the web may be offset or laterally offset towards one side of the slot or arranged closer to one of the legs than the other leg. The web may be located in one or both slots such that a cut blade can also be provided in one or both of the slots. The web may be located in one or both of the slots such that a cut blade can be moved or reciprocated in one or both of the slots without the cut blade contacting or interfering with the web.

The web may be fabricated from any sufficient material. Preferably, the web is rigid. Rigid may mean that the web is free from being elastic, flexible, compressible, bendable, or a combination thereof. In some configurations, however, the web may be elastic or flexible, or bendable.

The web may have a cross section that is generally straight. The web may have a cross-section that is bowed, curved, or not-straight or not-linear. For example, as shown in FIG. 3 of these figures, the cross-section of the web is partially bowed, curved, or not-straight or not-linear at a center location, and partially linear or not bowed or not curved at the top and bottom ends. A bowed, curved, irregular, non-linear, and/or not straight section or cross-section of the web may mean that that area curves or bows away from a center axis of the jaws or jaw assembly, while other portions, like top and bottom areas are not bowed or curved away from the center axis. Stated another way, a bowed or curved or non-linear section may be located further away from the center axis of the jaws or jaw assembly than other non-bowed, non-curved sections of the web, like either or both of the top and bottom ends. Stated another way, a bowed or curved or non-linear section may be located closer to one of the legs that define the slot, while the other section(s) of the web that are not bowed or curved are located further away from that same leg.

A bowed, curved, irregular, non-linear, and/or not straight section or cross-section of the web may advantageously provide for additional components, like a cut blade, to be positioned between the jaws without interfering with each other. That is, additional components like the cut blade may be arranged in the area that the web is curved or bowed or not straight so that the cut blade can be centrally located in the jaw assembly without contacting the web or any other components of the jaw assembly. A curved, bowed, irregular, non-linear or not straight cross-section may also advantageously provide for additional tissue blocking between the jaws, without requiring a thicker web, an additional web, or other tissue stops. That is, a bowed, curved, irregular, non-linear, or not-straight cross section web may provide additional surface area for blocking tissue from extending beyond a proximal edge or area of the jaw assembly as compared to if the cross section were generally straight or linear, for example. This curved, bowed, not-straight, or not-linear section may extend along an entire length of the web (i.e., from the proximal-most end of the web to the distal-most end of the web. Alternatively, the curved, bowed, not-straight, or not-linear section may be defined in only a distal portion or section of the web, while the rest of the web that is proximal of this curved section is generally flat, straight, or linear.

The web may be centrally located in the slot along the center plane or axis of the jaw or jaw assembly. A portion of the web (i.e., the upper or lower portions) may be aligned along the center plane or axis of the jaw or jaw assembly, while another portion of the web (i.e., the central portion) is laterally offset or bowed towards one of the legs defining the slot.

The web may be electrically conductive so that the web can participate in an electrosurgical circuit to electrically effect an object or anatomical feature. For example, the web may be energized and participate in a bipolar circuit with one or more of the jaws or jaw assembly for electrically effecting an object or anatomical feature. For example, the web may be energized and participate in a monopolar circuit with an external or ancillary electrode such as a remote or patient pad for electrically effecting an object or anatomical feature. If the web is an electrode and participates in a bipolar or monopolar circuit, then an insulating layer may be provided between the rib and the notch or slot where the web connects to the jaws to prevent short circuiting. The insulating layer may be provided on the jaws or rib, and/or the insulating layer may be provided on the web or notch. Alternatively, the web may be an insulator or non-electrically conductive.

The web may comprise a body portion. The body portion may function to attach the web to one or both of the jaws or anchoring sections. The body portion may include one or more features for connecting the web to one or more of the jaws. For example, the one or more features for attaching the web to one or both of the jaws or anchoring section may include a weld, adhesive, rivet, screw, bolt, or a combination thereof. The one or more features for attaching or connecting the web to one or both jaws or anchoring section(s) may be one or more notches.

The web may comprise a distal portion. The distal portion may be located distal of the body portion. The distal portion may be an extension of the body portion and have a same shape or cross section as the body portion. Alternatively, the distal portion may have flared ends such that the distal portion has a generally triangular shape. The flared ends may advantageously increase a surface area of the web to provide additional tissue blocking. A distal end or edge of the distal portion may be blunt. That is, a distal-most end or edge of the distal portion may be dull or not sharp such that the distal end or edge of the web cannot cut or transect an object or anatomical feature that comes in contact with the distal end or edge of the web. distal-most end of the web is located proximal to, or at a proximal end of, a gripping section of the jaw assembly.

An outline of the distal portion, the distal edge, the body portion, and/or the web may fit within an outline of the jaw assembly, the jaw shrouds, the flexing portions, the introducer or tubular member, or a combination thereof when the jaws are in a closed position. This means that an outer perimeter or outline of the web does not extend beyond or is free from extending or projecting beyond an outer perimeter of the jaw assembly, the jaw shroud, the flexing portions, the jaw assembly, the introducer or tubular member, or a combination thereof when the jaw assembly is in the closed position This also means that an outer perimeter of the web does not extend beyond or is free from extending or projecting beyond an outer perimeter of the jaw assembly, the jaw shroud, the flexing portions, the jaw assembly, the introducer or tubular member, or a combination thereof when the jaw assembly is in the open position. This advantageously ensures that the profile of the jaw assembly is slim for use in laparoscopic procedures and does not get caught or hung up on the surrounding environment (i.e., tissue, for example).

The body portion may comprise one or more notches. The notches may function to attach the web to one or more of the jaws and/or the anchoring sections. Preferably, the notches prevent movement of the web relative to one or both of the jaws, the jaw assembly, the hand piece, the cut blade, or a combination thereof, even when one or both of the jaws, gripping sections, cut blade, or a combination thereof are moved relative to the hand piece.

Each notch may be a cutout, a void, an absence of material, a depression, a groove, the like or a combination thereof. Each not can have any shape. For example, each notch can be circular, rectangular, square, oval, triangular, etc. Preferably, the body portion comprises two notches. The notches may be located anywhere on the body portion, along a length thereof. The notches may be located in an area that facilitate sufficient attachment to one or both of the jaws or anchoring portions.

Each notch may be located on an opposing side or edge of the web. Alternatively, more than one notch may be located on a side or edge of the web. One or both sides or edges of the web may include zero notches, one or more notches, two or more notches, three or more notches, etc.

Two of the notches may oppose each other. This means that the notches are located in the same general axial location between a proximal end and distal end of the web. Alternatively, the notches may be offset relative to one another, meaning that one notch is located further in a proximal or distal direction than another notch.

The instrument may include one or more cut blades. The cut blade may function to cut or transect an object or anatomical feature of interest, such as a vessel or tissue, for example. The cut blade may be a cutting blade or a scalpel. A distal end or edge of the cut blade may be sufficiently sharp to cut or transect an object or anatomical feature.

In some configurations, the cut blade may be connected to the power source so that the cut blade can function as an electrosurgical blade. For example, the cut blade may be energized and participate in a bipolar circuit with one or more of the jaws or jaw assembly for electrically effecting an object or anatomical feature. For example, the cut blade may be energized and participate in a monopolar circuit with an external or ancillary electrode such as a remote or patient pad for electrically effecting an object or anatomical feature.

In other configurations, the cut blade may not be connected to the power source or is electrically isolated from the power source; thus, the cut blade may be free from passing an electrical therapy current to effect an anatomical feature. In these configurations, the cut blade may be a mechanical cut blade.

The cut blade may be moved or reciprocated within one or both of the slots by moving or manipulating one or more of the user controls on the hand piece. The cut blade can be moved or extended to cut an anatomical feature captured between the jaw assembly (e.g., when the jaw assembly is in a closed or clamping position). The cut blade can be moved or extended beyond a distal end of the jaw assembly. The cut blade can be restricted or prevented from being moved or extending beyond a distal end of the jaw assembly. The cut blade may cut an anatomical feature after the anatomical feature is clamped and/or coagulated or sealed between the jaws of the jaw assembly. The cut blade may also cut an anatomical feature when the jaw assembly is in the open position.

The cut blade can be located between the jaws. The cut blade can be located in a slot between two opposing jaw elements. As was discussed above, the cut blade may be centered in a slot axis. The cut blade may be offset to one side of the slot axis (i.e., laterally offset from the center slot axis). The cut blade may be offset the slot axis towards one of the jaw elements.

FIG. 1 illustrates the instrument 10. The instrument 10 is a forceps. The instrument 10 comprises a hand piece 12; an introducer 14 connected to the hand piece; and a jaw assembly 16 extending through the introducer 14 and connected to the hand piece 12. The hand piece 12 comprises a number of user controls, including a lever 18, a trigger 20, a wheel 22, and a button 24. The instrument 10 may be in communication with a power source 26.

FIGS. 2 and 3 illustrate the jaw assembly 16. The jaw assembly 16 comprises a first jaw 28 and a second jaw 30. Each jaw 28, 30 comprises a respective gripping section 32, 34 and a respective anchoring section 36, 38 located proximal to the gripping sections 32, 34 relative to the hand piece 12 (FIG. 1). The gripping sections 32, 34 are adapted to effect an anatomical feature. Each of the gripping sections 32, 34 comprise a respective distal end 40a, 40b and respective proximal ends 42a, 42b. The anchoring sections 36, 38 are adapted to fixedly connect the respective jaw 28, 30 to the hand piece 12 such that the jaws 28, 30 are restricted from moving proximally or distally relative to the hand piece 12. Each jaw 28, 30 comprises a jaw shroud 84, 86.

The instrument 10 comprises a web 44 that is adapted to block an anatomical feature from extending beyond the proximal ends 42a, 42b of the gripping sections 32, 34 of the jaws 28, 30. A distal end or edge 60 of the web 44 is located generally at or near the proximal ends 42a, 42b of the gripping sections 32, 34 of the jaws 28, 30 (See also FIG. 5). The distal end or edge 60 of the web 44 is blunt, or not sharp.

The instrument 10 comprises a cut blade 46 that is adapted to cut or transect an anatomical feature located between the jaws 28, 30. As best illustrated in FIG. 3, a central portion 90 of the web 44 is bowed or curved away from a center axis or plane 94 of the jaw assembly 16 towards one side of the jaw assembly 16. The cut blade 46 may be positioned at or near the center portion 90 of the web 44 such that the cut blade 46 is generally aligned along the center axis 94 of the jaw assembly 16.

As discussed below, the web 44 is connected to one or both of the jaws 32, 34 such that the web 44 remains generally stationary relative to the hand piece 12 while the jaw assembly 16 and/or the cut blade 46 is moved relative to the hand piece 12.

Figure 4:
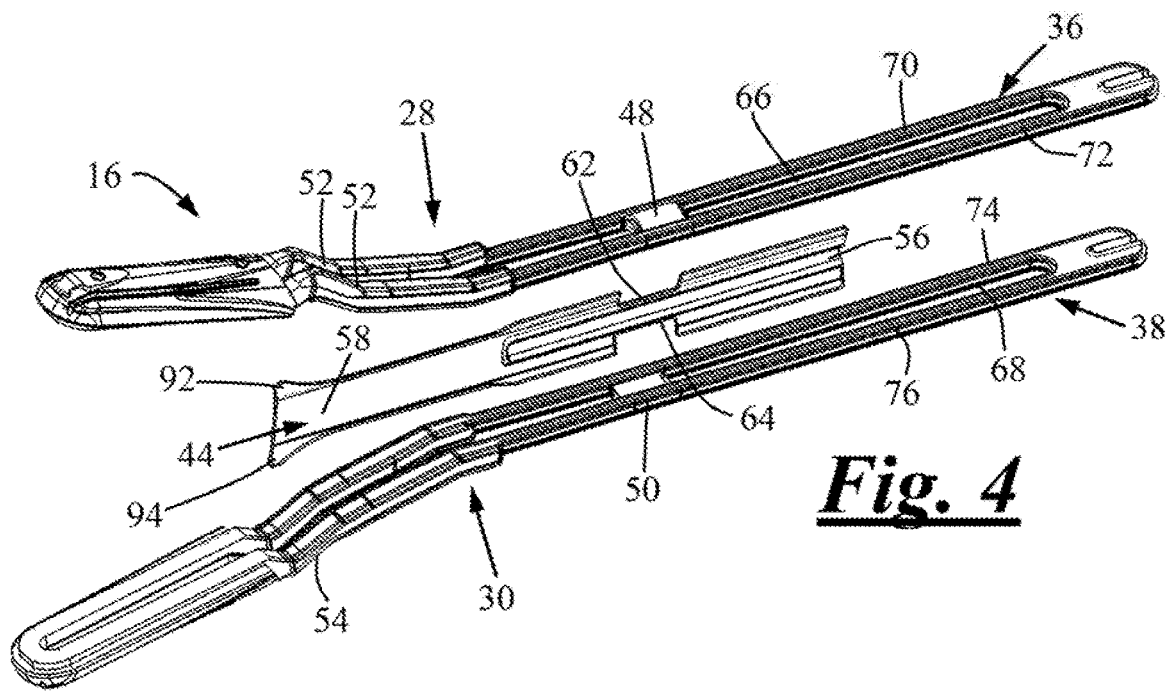
FIG. 4 is an exploded, perspective view of the jaw assembly with the cut blade removed for clarity.

FIG. 4 illustrates the jaw assembly 16 and the web 44. Each of the jaws 28, 30 comprise a respective slot 66, 68 defined between two opposing legs 70, 72 and 74, 76. The slots 66, 68 generally oppose each other. The slots 66, 68 extend from the anchoring sections 36, 38 to the gripping sections 28, 30. Each of the anchoring sections 36, 38 comprise a respective rib 48, 50 that spans the slot 66, 68 and connects the corresponding legs 70, 72 and 74,76. The ribs 48, 50 are generally aligned along a length of the jaws 28, 30 and generally oppose each other. Each of the anchoring sections comprise respective flexing portions 52, 54.

The web 44 comprises an elongated body portion 56 and a distal portion 58 located distal of the body portion 56. The body portion 56 comprises notches 62, 64. The notches 62, 64 are generally aligned along a longitudinal length of the web 44 and generally oppose each other. The distal portion 58 comprises ends 92, 94 that flare outwardly and away from the rest of the distal portion 58 and/or body portion 56. These flared ends 92, 94 provide additional surface area for the web 44 to block an anatomical feature.

The web 44 is connected to anchoring sections 36, 38 of the jaws 28, 30 by engaging the notches 62, 64 with the corresponding ribs 48, 50. Accordingly, the web 44 is at least partially located in one or both of the slots 66, 68. Moreover, due to the web 44 being connected to the jaws 28, 30 at the ribs 48, 50, the web 44 remains stationary relative to the handpiece 12 and the jaw assembly 16 when the jaw assembly 16 is moved between an open position (FIGS. 1-3 and 5) and a closed position (FIG. 6), as will be discussed further below. The distal portion 58 of the web 44 comprises a generally triangular shape.

Figure 5:
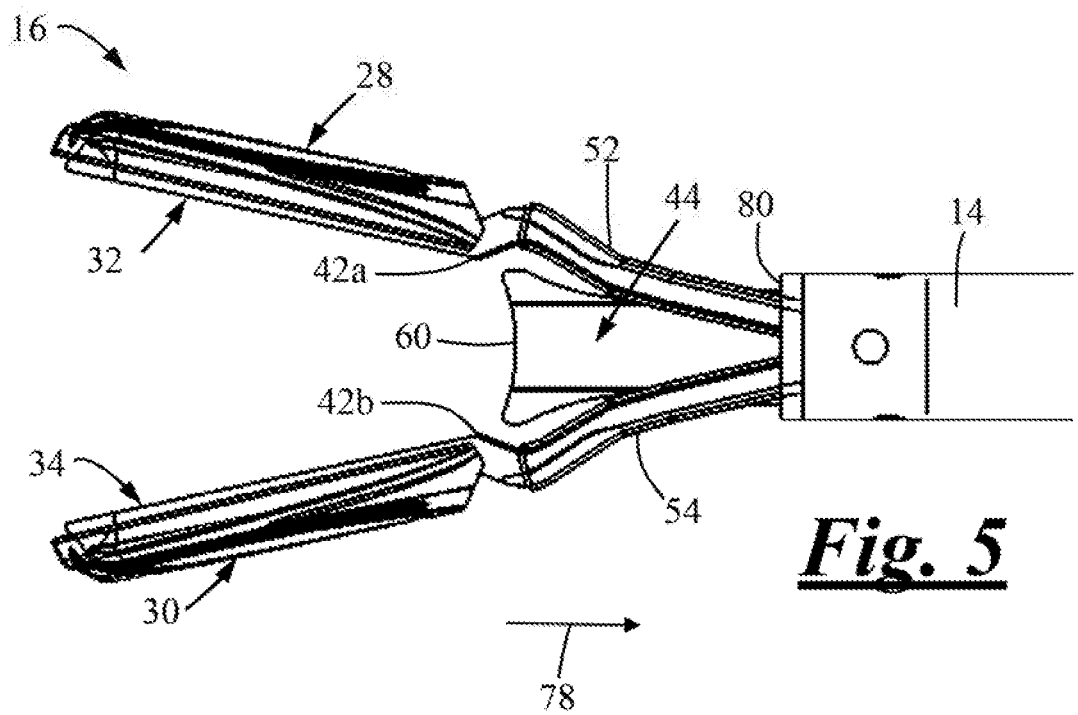
FIG. 5 is a side view of the jaw assembly in the open position.

FIG. 5 illustrates the jaw assembly 16 in the open position. To move the jaw assembly 16 into the open position from the closed position illustrated in FIG. 6, the introducer 14 is moved or retracted in a proximal direction 78 towards the hand piece 12 by manipulating one of the user controls on the hand piece 12, such as the lever 18. When the introducer 14 is moved or retracted in a proximal direction 78 towards the hand piece 12, a distal end 80 of the introducer is moved off of or away from the flexing sections 52 of the jaws 28, 30 thus allows the jaws 28, 30 to move away from one another into the open position. The open position may be a steady state position of the jaw assembly 16.

When the introducer 14 is moved or retracted in the proximal direction 78 towards the hand piece 12, the web 44 does not move. In other words, because the web 44 is attached to the ribs 48, 50 at the anchoring sections 36, 38, the web 44 remains generally stationary relative to the hand piece 12 and also generally stationary relative to the jaw assembly 16 when the jaw assembly 16 moves from the closed position to the open position.

Moreover, during the movement of the jaw assembly 16 from the closed position to the open position and/or while the jaw assembly 16 is in the open position, the cut blade 46 (not shown) may be moved in in either a proximal 78 or distal direction 82. When the cut blade 46 is moved, the web 44 remains stationary relative to the hand piece 12 and also stationary relative to the jaw assembly 16. The cut blade 46 can be moved in a proximal or distal direction by manipulating one of the user controls on the hand piece 12, such as the trigger 20.

The jaw assembly 16 may be rotated by manipulating one of the user controls, such as the knob 22. Because the web 44 is attached to both of the jaws 28, 30, the web 44 rotates with the jaw assembly 16 relative to the hand piece 12. The jaw assembly 16 may be rotated when the jaw assembly 16 is in the open position and/or in the closed position.

When the jaw assembly 16 is in the open position, the distal end 60 of the web 44 is located generally at or near the proximal ends 42a, 42b of the gripping sections 32, 34 of the jaws 28, 30 so that when an anatomical feature is located or positioned between the jaws 28, 30, the web 44 functions to block or prevent the anatomical feature from extending beyond the proximal ends 42a, 42b of a gripping sections 32, 34.

Figure 6:
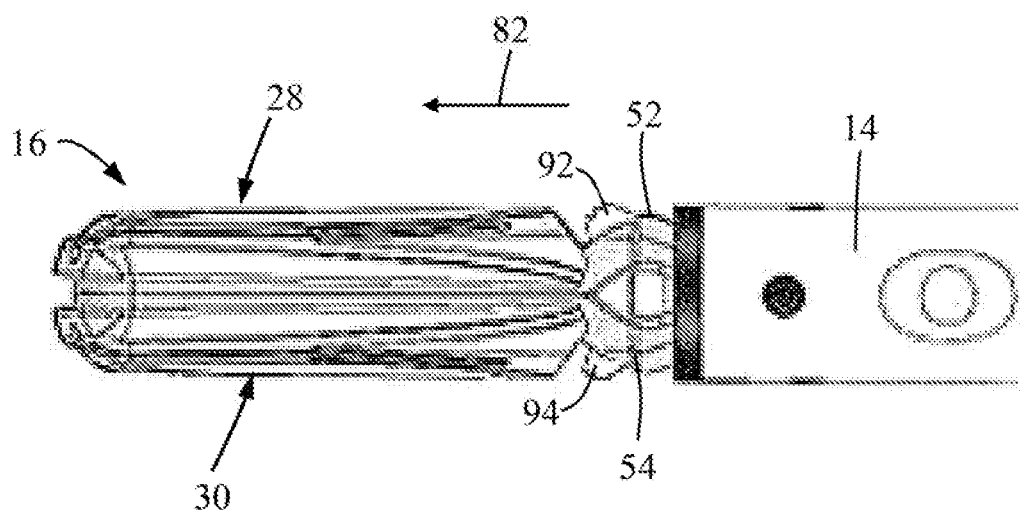
FIG. 6 is a side view of the jaw assembly in the closed position.

FIG. 6 illustrates the jaw assembly 16 in the closed position. When the introducer 14 is moved in the distal direction 82 away from the hand piece 12 such that the introducer 14 is moved onto the flexing sections 52, 54, the jaws 28, 30 are moved of flexed towards each other. When the introducer 14 is moved in a distal direction 82 away from the hand piece 12 and the jaws 28, 30 move to the closed position, the web 44 does not move. In other words, the web 44 remains generally stationary relative to the hand piece 12 and also the jaw assembly 16 when the jaw assembly 16 is moved into the closed position. During the movement of the jaws 28, 30 from the open to the closed position and/or while the jaw assembly 16 is in the closed position, the cut blade 46 (not shown) may be moved in in either a proximal 78 or distal direction 82. When the cut blade 46 is moved, the web 44 remains stationary relative to the hand piece 12 and also the jaw assembly 16.

As best illustrated in FIG. 6, when the jaw assembly 16 is in the closed position, the profile of the web 44, including the distal portion 58 and the ends 92, 94 and the distal end 60 (FIG. 4), are contained within a profile of the jaw assembly 16 and introducer 14. In other words, when the jaw assembly 16 is in the closed position, neither the web 44, nor the distal portion 58, nor the ends 92, 94, nor the distal end 60 extend or protrude beyond or outside of the jaw assembly 16, beyond or outside of the flexing portions 52, 54, beyond or outside of the jaw shrouds 84,86, beyond or outside of a diameter of the introducer 14, or a combination thereof.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The disclosures of all articles and references, including patent applications and publications, are incorporated by reference for all purposes.

Plural elements, ingredients, components or steps can be provided by a single integrated element, component or step. Alternatively, a single integrated element, component or step might be divided into separate plural elements, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

The invention claimed is:

1. Forceps comprising:
   a hand piece;
   a jaw assembly, the jaw assembly is moveable between an open position and a closed position, the jaw assembly comprises:
   a gripping section;
   an anchoring section located proximal to the gripping section, the anchoring section is adapted to connect the jaw assembly to the hand piece;
   a slot that extends along a length of the jaw assembly and is defined in the anchoring section and the gripping section, the slot including a rib that traverses the slot; and
   a web having a notch defined therein that engages the rib, wherein the web is located in the slot and is configured to remain stationary relative to the anchoring section, via the notch and the rib, while the jaw assembly is moved between the open position and the closed position.

2. The forceps according to claim 1, wherein the anchoring section is configured to move relative to the hand piece while the jaw assembly is moved relative to the hand piece.

3. The forceps according to claim 1, wherein the web is configured to be selectively energized to produce an electrosurgical blade.

4. The forceps according to claim 1, wherein a distal end of the web is blunt.

5. The forceps according to claim 1, wherein a portion of the web is bowed away from a center axis of the jaw assembly.

6. The forceps according to claim 5, wherein one or more portions of the web are generally aligned with the center axis of the jaw assembly.

7. The forceps according to claim 6, wherein the forceps comprise a cut blade.

8. The forceps according to claim 6, wherein one or more portions of the web are located proximal of the gripping section when the jaw assembly is in the closed position.

9. The forceps according to claim 1, wherein the web comprises an elongated body portion and a distal portion located distal of the body portion and the distal portion comprises ends that flare outwardly from the body portion.

10. The forceps according to claim 1, wherein the forceps comprise a cut blade that is moveable relative to the hand piece and the cut blade is located adjacent the web.

11. The forceps according to claim 10, wherein an outline of the web is contained within an outline of the jaw assembly when the jaw assembly is in the closed position.

12. The forceps according to claim 1, wherein the forceps comprise a tubular introducer, and when the jaw assembly is in the closed position a distal-most end of the web is located distal of a distal-most end of the introducer and proximal of a proximal-most end of the gripping section.

13. Forceps comprising;
    a hand piece;
    a jaw assembly connected to the hand piece, the jaw assembly comprises a first jaw and a second jaw, each of the jaws comprise a gripping section, an anchoring section, and a slot that is defined in the anchoring section of the first jaw and the second jaw, one of the slots including a rib that traverses the one of the slots;
    a web connected to the anchoring section of the first jaw and/or the second jaw, the web having a notch defined therein that engages the rib; and
    a cut blade;
    wherein the web is located in the one of the slots; and
    wherein the web remains stationary relative to the anchoring section via the notch and the rib, while the cut blade and the jaw assembly are moved relative to the hand piece.

14. The forceps according to claim 13 wherein the web has a distal-most end that terminates at a proximal end of each of the gripping sections to block an anatomical feature from extending beyond the proximal end of each of the gripping sections.

15. The forceps according to claim 13, wherein the web is laterally offset relative to a center plane of each of the slots.

16. The forceps according to claim 15, wherein the cut blade is aligned with a center plane of each of the slots.

17. The forceps according to claim 13, wherein the cut blade is aligned with a center plane of each of the slots.

* * * * *